(12) United States Patent
Leu

(10) Patent No.: US 6,726,674 B2
(45) Date of Patent: Apr. 27, 2004

(54) METHODS FOR MINIMALLY INVASIVE, LOCALIZED DELIVERY OF SCLEROTHERAPEUTIC AGENTS

(75) Inventor: Anders J. Leu, Baden (CH)

(73) Assignee: Jomed GmbH, Rangendingen (DE)

( * ) Notice: Subject to any disclaimer, the term of this patent is extended or adjusted under 35 U.S.C. 154(b) by 1 day.

(21) Appl. No.: 09/944,143

(22) Filed: Sep. 4, 2001

(65) Prior Publication Data

US 2003/0045860 A1 Mar. 6, 2003

(51) Int. Cl.$^7$ .............................................. A61M 31/00
(52) U.S. Cl. ..................... 604/508; 604/509; 604/101.1
(58) Field of Search .................. 604/500, 507–509, 604/96.01, 101.01–102.03, 103.01, 103.02, 103.06, 103.07, 915; 606/192, 194

(56) References Cited

U.S. PATENT DOCUMENTS

| | | |
|---|---|---|
| 4,423,725 A | 1/1984 | Baran et al. |
| 4,573,966 A | 3/1986 | Weikl et al. |
| 4,610,662 A | 9/1986 | Weikl et al. |
| 4,636,195 A | 1/1987 | Wolinsky |
| 4,655,746 A | 4/1987 | Daniels et al. |
| 4,708,718 A | 11/1987 | Daniels |
| 4,752,286 A * | 6/1988 | Okada .................. 604/506 |
| 4,776,349 A * | 10/1988 | Nashef et al. ............ 607/122 |
| 4,911,163 A | 3/1990 | Fina |
| 4,994,033 A | 2/1991 | Shockey et al. |
| 5,049,132 A | 9/1991 | Shaffer et al. |
| 5,087,244 A | 2/1992 | Wolinsky et al. |
| 5,090,960 A | 2/1992 | Don Michael |
| 5,135,484 A | 8/1992 | Wright |
| 5,213,577 A | 5/1993 | Kratzer |
| 5,232,444 A | 8/1993 | Just et al. |
| 5,328,471 A | 7/1994 | Slepian |
| 5,421,826 A | 6/1995 | Crocker et al. |
| 5,514,092 A | 5/1996 | Forman et al. |
| 5,558,642 A | 9/1996 | Schweich, Jr. et al. |
| 5,611,775 A | 3/1997 | Machold et al. |
| 5,772,632 A | 6/1998 | Forman |
| 5,785,679 A | 7/1998 | Abolfathi et al. |
| 5,833,658 A | 11/1998 | Levy et al. |
| 5,843,072 A | 12/1998 | Furumoto et al. |
| 5,951,458 A | 9/1999 | Hastings et al. |
| 6,048,332 A | 4/2000 | Duffy et al. |
| 6,126,635 A | 10/2000 | Simpson et al. |
| 6,143,015 A | 11/2000 | Nobles |
| 2002/0010418 A1 * | 1/2002 | Lary et al. ............. 604/101.04 |

* cited by examiner

Primary Examiner—LoAn H. Thanh
(74) Attorney, Agent, or Firm—Shinjyu Global IP Counselors, LLP.

(57) ABSTRACT

Apparatus and methods are provided for localized, minimally invasive administration of sclerotherapy in the treatment of varicose veins. A treatment site within a vein is isolated from blood flow through the vain. Sclerotherapeutic agents are delivered to the isolated vessel segment. A substantial portion of the agents are then removed from the vein, and isolation is removed from the treatment site. Inflammation, clotting, scarring, and closure of the varicose vein ensues at the treatment site. In a preferred embodiment, this technique is accomplished with a catheter having an inflatable member. The inflatable member is expandable to a deployed configuration in which its central region is of reduced cross-section as compared to its proximal and distal regions. The central region comprises one or more perforations extending through the inflatable member so that sclerotherapeutic agents may be delivered through the perforations.

18 Claims, 3 Drawing Sheets

METHODS FOR MINIMALLY INVASIVE, LOCALIZED DELIVERY OF SCLEROTHERAPEUTIC AGENTS

FIELD OF THE INVENTION

The present invention relates to delivery of therapeutic agents. More particularly, the present invention provides apparatus and methods for minimally invasive, localized delivery of sclerotherapeutic agents within a body lumen.

BACKGROUND OF THE INVENTION

Varicose veins are bulged sections of blue, twisted veins, normally found on a person's calf or thigh. In the United States alone, approximately 25 million people suffer from varicose veins. The condition is often hereditary and is most common in women. Onset may first occur during pregnancy, due to hormonal changes and increased pressure in the veins during uterus expansion. Obesity, menopause, aging, and repeated abdominal strain may also be contributing factors.

Veins carry oxygen-depleted blood back toward a person's heart. In a healthy persons one-way valves within the veins prevent backward flow of the blood away from the heart. In people with varicose veins, the valves may leak or may be absent, causing blood to accumulate and stretch the veins. Alternatively, weakness in the vein walls may cause pooling of the blood. Less commonly, congenital abnormalities or vascular diseases, such as phlebitis, may lead to accumulation. Regardless of the cause, the accumulated blood creates-unsightly lumps and kinks just under the skin.

In addition to cosmetic concerns, varicose veins may ache or itch, and may cause swelling and pain in the feet and ankles. Varicose veins tend to be progressive. Some affected people, especially those with more moderate symptoms, are able to reduce and/or control the condition through exercise, weight control, wearing of compression stockings, leg elevation, and/or avoidance of long periods of standing or sitting.

For more advanced cases, a variety of treatment options exist. The two most common are "sclerotherapy" and vein "stripping". Sclerotherapy seeks to close an affected vein, while vein stripping physically removes the vein. Veins blocked via sclerotherapy or removed via stripping have negligible adverse effect on blood flow through the body, as the legs provide many alternative paths for blood flow. Problems generally do not return to treated veins, but new varicose veins may develop at other locations. Less commonly, laser or electro-cautery treatments may be used; such treatments may lead to scarring or changes in skin color. Regardless of which treatment option is chosen, the goal is to eliminate "bad" veins and force blood to flow through alternative healthy veins.

Vein stripping is commonly performed under local or partial anaesthesia. A medical practitioner ties off a patient's affected vein above a varicose section. The practitioner then threads the distal end of a flexible device through the varicose section to a small incision near the patient's groin or ankle. The proximal end of the device is attached to the varicose section. The practitioner then pulls the flexible device out of the patient through the incision, bringing with it, or "stripping", the varicose vein. Connecting veins that attach to deeper veins are tied off.

Vein stripping has been in clinical use since the 1950's. Anaesthesia-related complications, including nausea and vomiting, may occur. Due to the invasiveness of the procedure, wound infection or scarring may be observed at the point of incision, and blood clots occasionally form.

Sclerotherapy involves insertion of a fine needle into a varicose vein. A therapeutic substance is injected through the needle directly into the vein. The sclerotherapeutic agent irritates an internal lining of the vein, causing inflammation, and, eventually, blood clotting and scarring that permanently blocks the vein. The body absorbs accumulated blood within the vein, and unsightly lumps flatten out over time. After injection, tissue surrounding the vein is wrapped in compression bandages for several days. Patients whose legs have been treated generally undertake a walking regimen to force blood to find alternative pathways, and to prevent blood clots distant from the point of treatment. Patients usually require multiple sclerotherapy treatment sessions.

Sclerotherapy and derivative methods have been in use since the 1920's. Common sclerotherapeutic agents include hypertonic saline, sodium tetradecyl sulfate ("Sotradecol"), and aethoxyskerol ("Polidocanol"). Complications may depend on the agent injected into the vein. Sotradecol triggers allergic reactions in some patients, occasionally severe. Hypertonic saline solution is less likely to cause allergic reactions, but either agent may burn the patient's skin if the needle is not properly inserted, or may permanently mark or "stain" the skin.

A major drawback of current sclerotherapy techniques is that the injected agent is not localized at a treatment site, thereby reducing the efficacy of treatment and increasing systemic delivery of the agent. Occasionally, such systemic delivery leads to dangerous blood clot formation distant from the point of treatment.

In view of the drawbacks associated with previously known techniques for treating varicose veins, it would be desirable to provide apparatus and methods that overcome these drawbacks.

It would be desirable to provide methods and apparatus that reduce or eliminate blood clotting distant from a treatment site.

It also would be desirable to provide apparatus and methods for treating varicose veins that are localized and minimally invasive.

It would be desirable to provide apparatus and methods that reduce a quantity of foreign substances left in the body post-treatment.

SUMMARY OF THE INVENTION

In view of the foregoing, it is an object of the present invention to provide apparatus and methods for treating varicose veins that overcome the drawbacks of previously known techniques.

It is an object to reduce or eliminate blood clotting distant from a treatment site.

It is another object to provide apparatus and methods that are localized and minimally invasive.

It is yet another object of the present invention to reduce a quantity of foreign substances left in the body.

These and other objects are accomplished by providing apparatus comprising a catheter having an inflatable member for localized delivery of therapeutic agents. The catheter may be as described, for example, in U.S. Pat. No. 5,833,658 to Levy et al., or U.S. Pat. No. 5,611,775 to Machold et al. both of which are incorporated herein by reference.

In a preferred embodiment, the catheter has a guide wire lumen extending between its proximal and distal ends, and an inflation lumen extending between its proximal end and the inflatable member. The inflatable member comprises proximal and distal regions, and a central region disposed therebetween. The inflatable member is reversibly expandable from a collapsed delivery configuration to an expanded deployed configuration.

The central region of the inflatable member has a reduced cross-section in the deployed configuration, as compared to the proximal and distal regions. The central region further comprises one or more perforations extending through the inflatable member. When the inflatable member has been fully expanded to the deployed configuration via an inflation fluid delivered through the inflation lumen of the catheter, additional injection of a volume of the fluid causes a substantially equal volume of the fluid to exit through the one or more perforations.

When deployed in a blood vessel at a treatment site, the proximal and distal regions of the inflatable member sealingly engage an interior wall of the vessel, establishing an isolated vessel segment in the vicinity of the central region. Continued injection of the inflation fluid post-engagement of the vessel wall provides localized delivery of the inflation fluid to the isolated segment. Upon collapse of the inflatable member back to the delivery configuration by withdrawing the inflation fluid through the inflation lumen, a substantial portion, for example, a majority, of the inflation fluid delivered to the isolated segment is also withdrawn from the vessel through the perforations in the central region.

When the inflation fluid comprises a sclerotherapeutic agent, localized, minimally invasive sclerotherapy is achieved. The apparatus of the present invention may alternatively be used to locally deliver therapeutic agents to an isolated vessel segment in a variety of other intraluminal clinical applications, for example, to treat stenosis or restenosis.

Methods of using the apparatus of the present invention are also provided.

BRIEF DESCRIPTION OF THE DRAWINGS

Further features of the invention, its nature and various advantages will be more apparent from the following detailed description of the preferred embodiments, taken in conjunction with the accompanying drawings, in which like reference numerals apply to like parts throughout, and in which.

DETAILED DESCRIPTION OF THE INVENTION

The present invention provides apparatus and methods for localized, minimally invasive delivery of therapeutic agents. More specifically, the present invention provides improved methods and apparatus for performing sclerotherapy.

Figure 1A:
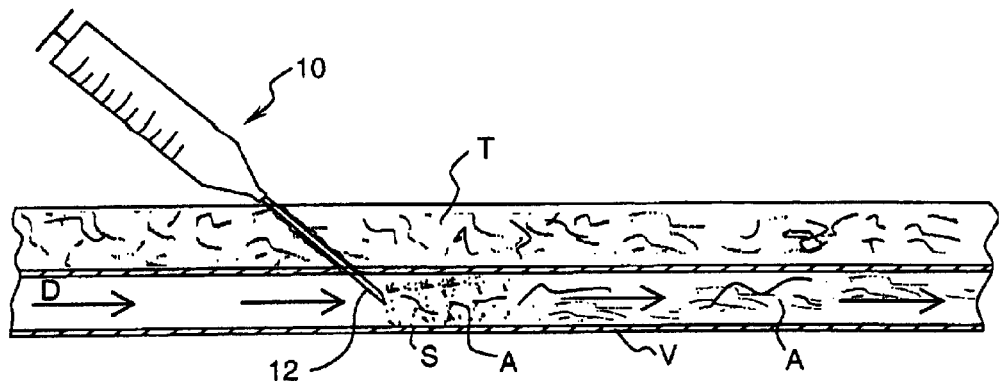
FIGS. 1A–1C are side-sectional views or a prior art method of performing sclerotherapy.
Figure 1B:
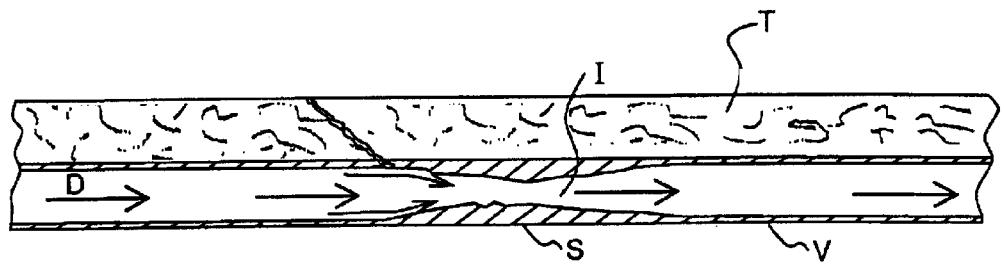
Figure 1C:
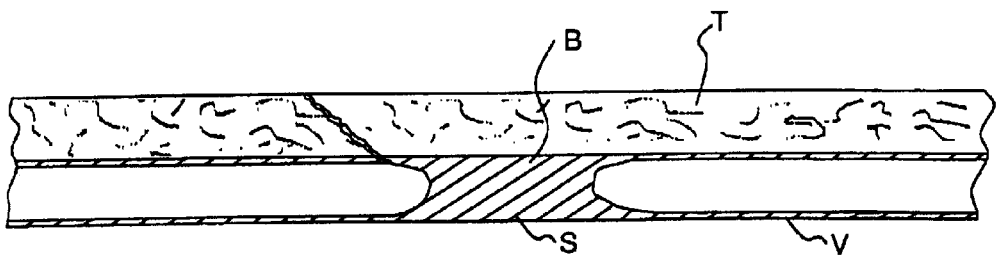

With reference to FIGS. 1A–1C, a prior art method of performing sclerotherapy is described. A medical practitioner seeks to treat varicose vein V by blocking blood flowing in direction D through the vessel at treatment site S. As seen in FIG. 1A, needle 12 of syringe 10 is advanced through tissue T into the lumen of varicose vein V. A bolus of sclerotherapeutic agent A is injected through needle 12 directly into the vein in the vicinity of treatment site S. Agent A may comprise, for example, hypertonic saline, sodium tetradecyl sulfate ("Sotradecol"), or aethoxyskerol ("Polidocanol"). After injection of the agent, syringe 10 and needle 12 are removed from the patient.

As seen in FIG. 1B, sclerotherapeutic agent A irritates an internal lining of the vein, causing inflammation I. Eventually, as seen in FIG. 1C, blood clotting and scarring occurs that creates permanent veinous block B at treatment site S within varicose vein V. Over time, the body absorbs accumulated blood within vein V, and unsightly lumps flatten out. Blood flow continues through alternative pathways.

The method described with respect to FIGS. 1A–1C has several drawbacks. If needle 12 is not properly inserted within varicose vein 7, sclerotherapeutic agent A may burn the patient's skin, or may permanently mark or "stain" the skin. Additionally, agent A is not localized at treatment site S. Rather, as seen in FIG. 1A, blood flowing in direction D through vessel V carries a substantial portion of agent A to downstream vasculature. Treatment efficacy is thereby reduced, and a larger volume or a higher concentration of agent A may be required to ensure formation of veinous block B. Systemic delivery of the agent via blood flow occasionally may yield blood clot formation distant from treatment site S. Such blood clots may require emergency surgery and may lead to limb amputation or even death.

Referring now to FIGS. 2A–2D, apparatus in accordance with the present invention is described. Apparatus 20 comprises catheter 22 and inflatable member 24. Inflatable member 24 is affixed to the exterior surface of catheter 22 at connection regions 23 and 25. Radiopaque marker sands 21, fabricated, for example, from gold, platinum, or tantalum, are attached to catheter 22 between connection regions 23 and 25 to facilitate proper positioning of inflatable member 24 within a patient's vessel.

Catheter 22 comprises proximal end 26, distal end 28, and guide wire lumen 30 extending therebetween to allow blood to flow between the proximal and distal ends 26 and 28. Catheter 22 further comprises inflation lumen 32 extending from proximal end 26 to a position distal of connection region 23. Inflation lumen 32 is in fluid communication with the interior of inflatable member 24. In FIG. 2C, catheter 22 is illustratively shown as dual-lumen; however, it will be apparent to those of skill in the art that inflation lumen 32 alternatively may comprise a tube separate from catheter 22.

Inflatable member 24 comprises proximal region 34, distal region 36, and central region 35 disposed therebetween. Inflatable member 24 preferably comprises a diameter of between about 4 mm and 8 mm in the collapsed delivery configuration of FIG. 2A. Furthermore, inflatable member 24 preferably comprises a length of approximately 40 mm, with central region 35 extending over about one half that length. Central region 35 comprises one or more perforations 38 extending through inflatable member 24. In FIG. 2D, inflatable member 24 is illustratively shown with a plurality of perforations 38 disposed radially about the inflatable member. Alternatively, a longitudinal spacing, a combination of longitudinal and radial spacing, or any other spacing pattern may be provided for perforations 38. Additionally, a different quantity of perforations may be provided.

Figure 2A:
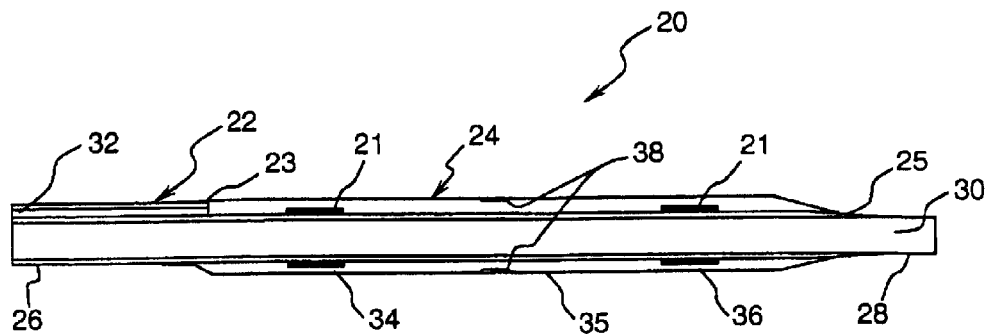
FIGS. 2A–2D are views of an embodiment of apparatus of the present invention, shown, respectively, in side-section in a collapsed delivery configuration and in an expanded deployed configuration, and in cross-section along view lines A—A and B—B of FIG. 2B.
Figure 2B:
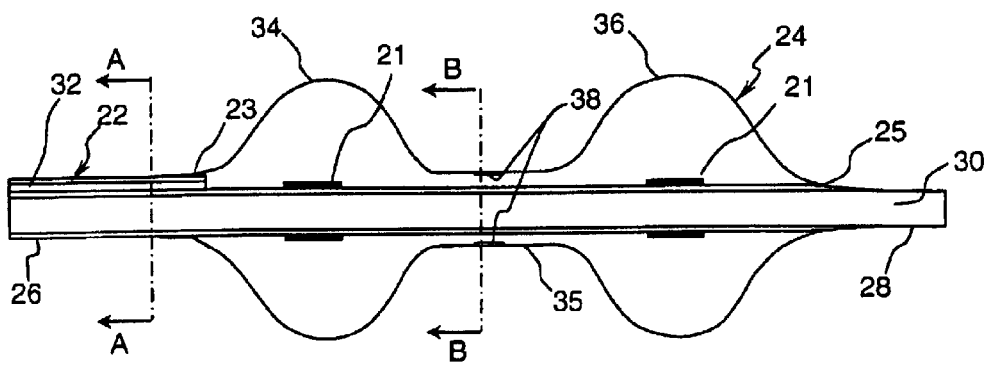
Figure 2C:
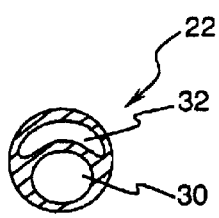
Figure 2D:
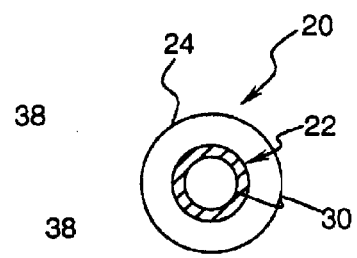

Inflatable member 24 is reversibly expandable from the collapsed delivery configuration of FIG. 2A to the expanded deployed configuration of FIG. 2B. As seen in FIG. 2B, central region 35 of inflatable member 24 comprises a reduced cross-sectional area in the deployed configuration as compared to proximal region 34 and distal region 36. The reduced cross-section may be achieved by any of a variety of techniques. For example, heat may be applied to central section 35 to reduce its cross-section. Alternatively, a specialized blow mold may be used to form inflatable member 24 with central section 35 in a single step.

Upon full expansion of inflatable member 24 via an inflation fluid delivered through inflation lumen 32 of catheter 22, additional injection of a volume of inflation fluid is expected to cause a substantially equal volume of inflation fluid to exit through the one or more perforations 38. As seen in FIG. 2A, using inflation lumen 32 for both expansion of inflatable member 24 and injection of inflation fluid through perforations 38 provides a very small delivery profile suitable for use in small vasculature. However, during expansion of the inflatable members a portion of the inflation fluid my escape from the inflatable member through perforations 38. Thus, an injection lumen coupled to the perforations may be provided to ensure that no fluid is delivered through perforations 38 until inflatable member 24 is in the fully deployed configuration. Additionally, an injection lumen may provide more precise control over the volume of fluid delivered through perforations 38.

Figure 3A:
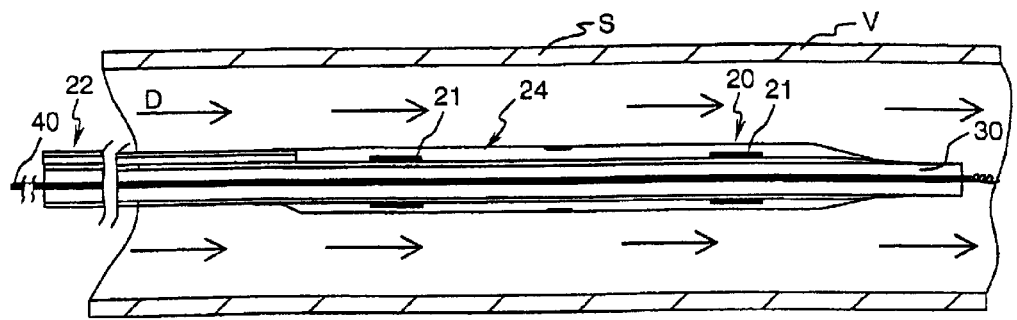
FIGS. 3A–3D are side-sectional views of the apparatus of FIG. 2 within a patients vasculature, illustrating a method of using the apparatus in accordance with the present invention.

With reference now to FIGS. 3A–3D, a method of using apparatus 20 in the treatment of varicose veins is described. In FIG. 3A, a medical practitioner seeks to close varicose vein V at treatment site S. Blood flows through vein V in direction D. Using well-known percutaneous techniques, guide wire 40 is advanced through vein V to a position distal of treatment site S. Apparatus 20 is then advanced over wire 40 via guide wire lumen 30 until radiopaque marker bands 21 are disposed on either side of treatment site S, as may be determined, for example, with a fluoroscope. Rapid exchange-type advancement may alternatively be employed.

Figure 3B:
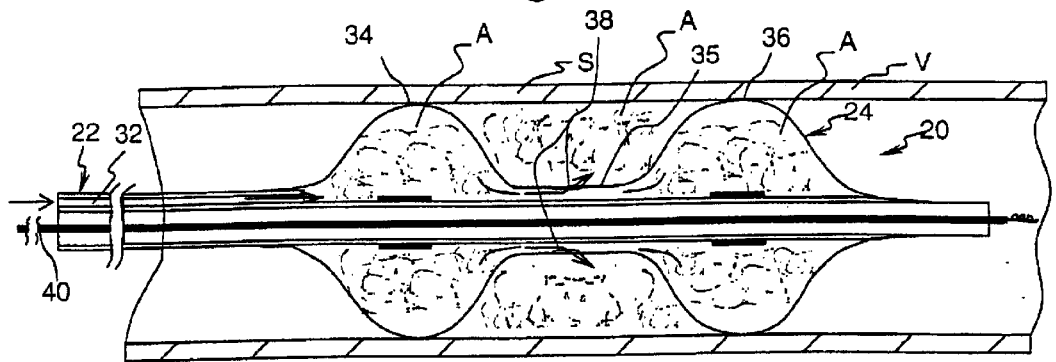

In FIG. 3B, once apparatus 20 has been properly positioned, sclerotherapeutic agent A is injected through inflation lumen 32 into the interior of inflatable member 24. As described hereinabove, agent A may comprise, for example, hypertonic saline, Sotradecol, Polidocanol, or an alcohol solution. Agent A may alternatively comprise any substance that achieves closure of varicose vein V.

Upon full expansion of inflatable member 24, proximal region 34 and distal region 36 of the inflatable member sealingly engage the interior wall of vein V, thereby isolating a segment of the vein disposed about central region 35 at treatment site S. Additional injection of a volume of sclerotherapeutic agent A is expected to cause a substantially equal volume of the agent to exit through perforations 28 into the isolated vessel segment, thereby providing localized delivery of agent A to the isolated segment. Inflatable member 24 is maintained in the expanded deployed configuration for a period of time adequate to cause initial inflammation, clotting, or scarring within varicose vein V at the treatment site.

Figure 3C:
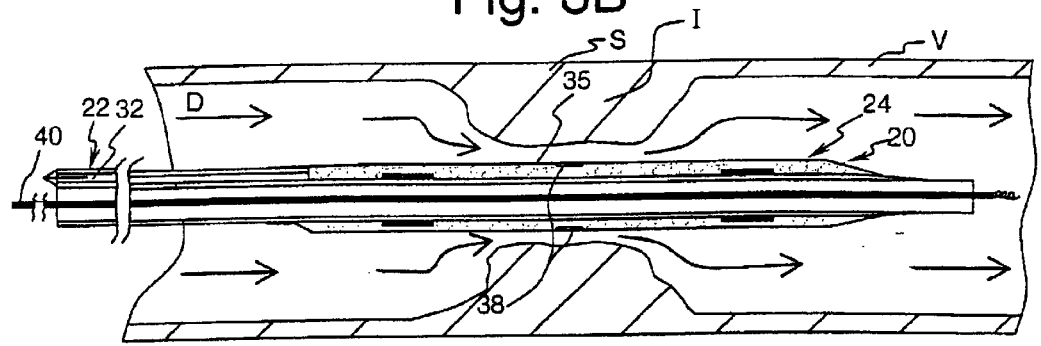

In FIG. 3C, once inflammation I has initiated, inflatable member 24 is collapsed back to the delivery configuration by withdrawing sclerotherapeutic agent A through inflation lumen 32. A substantial portion, for example, a majority, of agent A delivered to treatment site S of varicose vein V is also withdrawn from the vein through perforations 38 in central region 35 during collapse of the inflatable member.

In the context of the present invention, "a substantial portion" of agent A means a portion sufficient to reduce clotting distant from the treatment site. Thus, the present invention reduces a risk of clotting distant from the treatment site, as compared to the sclerotherapy technique described with respect to FIGS. 1A–1C.

Figure 3D:
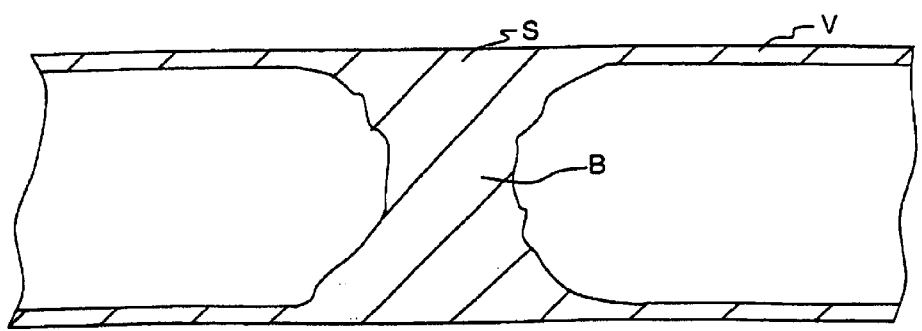

In FIG. 3D, upon collapse of inflatable member 24 back to the delivery configuration, apparatus 20 and guide wire 40 are removed from the patient's vasculature. Inflammation, blood clotting and scarring progress until permanent veinous block B forms at treatment site S within varicose vein V. Flow through the vein halts. Over time, the body absorbs accumulated blood within the vein, and unsightly lumps flatten out. Blood flow continues through alternative pathways.

The present invention provides localized, minimally invasive delivery of therapeutic agents at a treatment site within a body lumen. As compared to previously known sclerotherapy techniques, a significantly higher concentration of sclerotherapeutic agents may be delivered directly to the treatment cite. Additionally, the agents may be kept in residence at the treatment site for a length of time defined by a medical practitioner, rather than by flow conditions within the vessel. Further still, since it is expected that a substantial portion of the agents will be aspirated from the patient prior to completion of the procedure, the patient's systemic exposure to the agents is decreased. For these and other reasons, significant efficacy benefits are expected.

While preferred illustrative embodiments of the present invention are described hereinabove, it will be apparent to those of skill in the art that various changes and modifications may be made therein without departing from the invention. For example, apparatus 20 may further comprise a perfusion lumen to allow uninterrupted blood flow during delivery of therapeutic substances. An isolated vessel segment may be obtained by using two separate inflatable members attached to catheter 22 in spaced-apart relation. Additionally, agents other than sclerotherapeutic agents may be delivered, for example, chemotherapy agents, clotting or anti-clotting agents, radioactive agents, gene vectors, medicaments, etc. The appended claims are intended to cover all such changes and modifications that fall within the true spirit and scope of the invention.

What is claimed is:

1. A method of administering sclerotherapy to a varicose vein, the method comprising:

isolating a segment of the varicose vein from blood flow through the vein;

delivering sclerotherapeutic agents to the isolated segment, thereby initiating occlusion of the vein;

removing from the varicose vein a substantial portion of the sclerotherapeutic agents delivered to the isolated segment; and then removing isolation from the vein segment.

2. The method of claim 1, wherein the substantial portion comprises a majority of the sclerotherapeutic agents delivered to the isolated segment.

3. The method of claim 1, wherein the sclerotherapeutic agents are chosen from the group consisting of hypertonic saline, sodium tetradecyl sulfate, and aethoxyskerol.

4. The method of claim 1, wherein isolating the segment of the varicose vein comprises expanding first and second inflatable members proximal and distal of the vein segment, respectively.

5. A method of administering sclerotherapy to a varicose vein, the method comprising:

providing an apparatus comprising a catheter and a inflatable member, the catheter having an inflation lumen coupled to the inflatable member;

the inflatable member reversibly expandable from a collapsed, delivery configuration to an expanded, deployed configuration, the inflatable member having proximal and distal regions, and a central region disposed therebetween;

the central region having a reduced cross-section, as compared to the proximal and distal regions, in the deployed configuration, the central region further comprising at least one perforation extending through the inflatable member;

isolating a segment of the varicose vein from blood flow through the vein by expanding the inflatable member from the delivery configuration to deployed configuration;

delivering sclerotherapeutic agents to the isolated segment through the at least one perforation, thereby initiating occlusion of the vein removing a substantial portion of the sclerotherapeutic agents delivered to the isolated segment; and then removing isolation from the vein segment.

6. The method of claim 5, wherein expanding the inflatable member comprises sealingly engaging an interior surface of the varicose vein proximally and distally of the vein segment with the proximal and distal regions of the inflatable member, respectively.

7. The method of claim 5, wherein expanding the inflatable member comprises injecting sclerotherapeutic agents through the inflation lumen of the catheter.

8. The method of claim 5, wherein delivering sclerotherapeutic agents to the isolated segment comprises injecting an additional volume of the sclerotherapeutic agents through the inflation lumen after the inflatable member has been expanded to the deployed configuration, thereby causing a portion of the sclerotherapeutic agents to pass through the at least one perforation in the central region of the inflatable member.

9. The method of claim 5, wherein removing isolation from the vein segment comprises collapsing the inflatable member back to the delivery configuration.

10. The method of claim 9, wherein collapsing the inflatable member back to the delivery configuration comprises removing the sclerotherapeutic agents form the inflatable member through the inflation lumen.

11. The method of claim 9 further comprising removing the apparatus from the varicose vein.

12. The method of claim 5 further comprising, prior to removing isolation from the vein segment, removing from the varicose vein a substantial portion of the sclerotherapeutic agents delivered to the isolated segment.

13. The method of claim 12, wherein removing the substantial portion of the sclerotherapeutic agents comprises removing the agents from the isolated segment through the at least one perforation and through the inflation lumen.

14. The method of claim 5, wherein the catheter further comprises a guide wire lumen, and wherein isolating the vein segment further comprises:

prior to expanding the inflatable member, advancing a guide wire to the vein segment using well-known percutaneous techniques; and advancing the catheter over the guide wire to the vein segment via the guide wire lumen.

15. The method of claim 5, wherein the apparatus further comprises an infusion lumen coupled to the at least one perforation extending through the inflatable member, and wherein delivering sclerotherapeutic agents to the isolated segment comprises injecting sclerotherapeutic agents through the infusion lumen.

16. A The method of claim 15, wherein removing the substantial portion of the sclerotherapeutic agents comprises removing the agents from the isolated segment through the at least one perforation and through the infusion lumen.

17. The method of claim 5, wherein the apparatus further comprises an additional lumen extending axially across the inflation lumen to allow blood to flow therethrough.

18. The method of claim 17 further comprising maintaining blood flow through the varicose vein while the vein segment is isolated by flowing the blood through the additional lumen.

* * * * *